United States Patent [19]

Cunningham et al.

[11] Patent Number: 5,283,186
[45] Date of Patent: Feb. 1, 1994

[54] PREPARATION OF A COMPRESSED MEMBRANE CONTAINING IMMOBILIZED BIOLOGICALLY ACTING MATERIAL

[75] Inventors: David D. Cunningham, Lakemoor; Kenneth S. Johnson, Buffalo Grove, both of Ill.

[73] Assignee: Abbott Laboratories, Abbott Park, Ill.

[21] Appl. No.: 815,422

[22] Filed: Dec. 31, 1991

[51] Int. Cl.$^5$ .............. C12N 11/08; C12N 11/04; G01N 33/545; G01N 33/544
[52] U.S. Cl. .................... 435/180; 435/182; 436/531; 436/535; 530/815; 530/817
[58] Field of Search ........... 435/177, 180, 182; 436/531, 535; 530/815, 817

[56] References Cited

U.S. PATENT DOCUMENTS

| | | | |
|---|---|---|---|
| 4,070,348 | 1/1978 | Kraemer et al. | 435/180 X |
| 4,073,713 | 2/1978 | Newman | 204/195 B |
| 4,240,889 | 12/1980 | Yoda et al. | 204/195 B |
| 4,276,141 | 6/1981 | Hawkins | 204/195 B |
| 4,321,123 | 3/1982 | Nakamura et al. | 204/195 B |
| 4,376,689 | 3/1983 | Nakamura et al. | 204/195 B |
| 4,388,166 | 6/1983 | Suzuki et al. | 204/403 |
| 4,415,666 | 11/1983 | D'Orazio et al. | 435/179 |
| 4,454,007 | 6/1984 | Pace | 204/1 T |
| 4,486,292 | 12/1984 | Blackburn | 204/416 |
| 4,549,951 | 10/1985 | Knudson et al. | 204/416 |
| 4,579,642 | 4/1986 | Niiyama et al. | 204/403 |
| 4,759,828 | 7/1988 | Young et al. | 204/1 T |
| 4,788,146 | 11/1988 | King et al. | 435/72 X |
| 4,808,529 | 2/1989 | Doppelfeld et al. | 435/179 |
| 4,889,612 | 12/1989 | Geist et al. | 204/416 |
| 4,894,339 | 1/1990 | Hanazato et al. | 435/182 |
| 4,895,806 | 1/1990 | Le et al. | 435/288 |
| 4,975,375 | 12/1990 | Haruta et al. | 435/182 |

FOREIGN PATENT DOCUMENTS 2194843A 3/1988 United Kingdom .

*Primary Examiner*—David M. Naff
*Attorney, Agent, or Firm*—Robert F. Wexler

[57] ABSTRACT

A porous carrier containing an immobilized biologically active material is prepared in which a relatively large amount of an enzyme or an antibody has been immobilized in a manner that produces a low diffusion resistance toward reagents and products. The porous carrier is produced by fixing enzymes or antibodies within internal micropores of the carrier and mechanically compressing the carrier to a final thickness which is in the range of about 0.20 to 0.80 times the uncompressed carrier thickness. The compressed carrier may have a density about 1.25 to about 5.0 times the density of the carrier before compressing. Surprisingly, the compressed carrier exhibits less diffusion resistance to specific reagents and products than would an uncompressed carrier. A preferred porous carrier is a semipermeable membrane made from synthetic polymers, such as polyvinylidine difluoride.

14 Claims, No Drawings

PREPARATION OF A COMPRESSED MEMBRANE CONTAINING IMMOBILIZED BIOLOGICALLY ACTING MATERIAL

FIELD OF THE INVENTION

The invention relates generally to the field of catalysis by biologically active materials. More particularly, the invention relates to immobilized proteins attached to porous carriers. The invention concerns proteins, such as enzymes, antibodies, and enzyme-antibody conjugates.

BACKGROUND OF THE INVENTION

Biologically active materials, such as proteins, are important catalysts for industrial and analytical chemistry because they are highly specific to particular reagents and because they exhibit high catalytic activity and speed of reaction. Enzymes, antibodies, and enzyme-antibody conjugates are sub-classes of proteins. However, biologically active proteins are often difficult to isolate and expensive to make and use. It is usually desirable to utilize proteins in an immobilized form in which biologically active proteins are attached to a solid carrier which confines the active proteins and permits their reuse. Several means of immobilizing biologically active proteins on solid carriers are known, such as adsorption, ionic bonding, entrapment, and covalent bonding.

Proteins, of which enzymes and antibodies are subclasses, are relatively large molecules that contain positively charged, negatively charged, and uncharged non-ionic portions. Ionicly bound proteins are produced when a charged portion of the protein comes in close contact to an oppositely charged portion of a solid carrier surface. Under many conditions this attachment is irreversible. Adsorptively bound proteins are produced when the uncharged portion of the protein comes in close contact to an uncharged, non-ionic portion of a solid carrier surface. Several ionic and adsorptive attachments may be necessary to irreversibly bind a single protein.

Covalent bonds that immobilize proteins are formed by linking amino or carboxyl groups, which are present in every enzyme, with polar functional groups attached to the carrier. The functional groups can be derived from components normally present in the material that forms a carrier substrate or the functional groups can be added to the carrier. Suitable functional groups include carboxyl groups, amino groups, sulphonic acid groups, imino groups, thio groups, hydroxyl groups, azo groups, epoxy groups, aldehyde groups, acid chloride groups, activated carbonyl groups, pyridyl groups, and phosphoryl groups. The functional groups may be further activated by chemical treatment to enhance their ability to join with the amino or carboxyl groups present in the protein molecules.

Known techniques for covalently immobilizing proteins on porous carriers have significant limitations. For example, large amounts of biologically active material can be immobilized inside a bulk carrier, such as a block of porous material or thick porous membrane, but the depth and physical properties of the protein layers so immobilized are difficult to control. Also, diffusion into and out of blocks and relatively thick membranes is slow.

By another technique, biologically active material, such as enzymes, antibodies, or enzyme-antibody conjugates can be immobilized in small amounts as a thin layer inside thin membranes or as a thin layer on the surface carrier membranes, but the limited amount of biologically active material which can be deposited into the thin layers is often insufficient to carry out a desired chemical reaction. Further, biological materials tend to deactivate over time and a carrier with only a small amount of active material may not function over a period of time long enough to be practical.

BRIEF SUMMARY OF THE INVENTION

The present invention is directed to a new carrier for biologically active materials, such as proteins, which can hold more of the active material in a well-defined, thin layer than was previously possible. Alternately, the new carrier may be utilized to present a thin layer of the biologically active material with exceptionally low diffusion resistance According to the instant invention, the carrier is compressed to produce a thinner and more concentrated immobilized layer of the active material Surprisingly, compression of the porous carrier makes the active material inside the carrier relatively more reactive. The active material located within internal micropores is subject to less diffusion resistance toward specific reagents when the carrier is in a compressed state. Even though access to some of the active material in the carrier substrate may be restricted by the collapse of some connecting micropores, compression of the carrier increases overall mass transfer to and from the biologically active material. It is preferred that the biologically active material be a protein, such as an enzyme or an antibody.

In one aspect of the invention, the carrier material is a porous membrane fashioned from a synthetic polymer material. The pores in such polymer material are not oriented in one particular direction. Individual pores need not extend completely through the membrane. Instead, the micropores of synthetic polymers can be randomly oriented and often wind irregularly through and terminate within the carrier substrate. Such synthetic polymer membranes may be compressed until they measure only about 0.20 times their original thickness and still exhibit decreased diffusion resistance to desirable reagent molecules.

In a preferred form, the invention is a porous carrier for immobilized proteins which comprises a compressed substrate having an internal surface which defines a plurality of micropores distributed throughout the substrate. A plurality of functional groups are attached to the internal surface of the substrate, and a plurality of catalytically selective protein molecules are covalently attached to at least a portion of the functional groups. Said compressed substrate exhibits a diffusion resistance which is less than the diffusion resistance exhibited by said substrate in an uncompressed state, with respect to a reagent for which the protein molecules are catalytically selective.

The protein may be any biologically reactive material, such as glucose oxidase, urease or an antibody. It is preferred that the substrate be compressed after the protein is attached to the functional groups. The carrier may be in contact with a stabilizing liquid solution while the substrate is compressed. Compression of the carrier substrate may increase substrate density by a factor within the range of about 1.25 to about 5.0 and still demonstrate the surprising decrease in diffusion resistance of the instant invention.

DETAILED DESCRIPTION OF THE PREFERRED EMBODIMENTS

Proteins are biologically active materials. Enzymes are a subclass of proteins. As proteins, enzymes contain peptide chains composed of a large number of amino acid derivatives, each linked to adjacent acid derivatives through a carboxyl group on one side and an amine group on the other. The peptide chains are wrapped or coiled into distinctive shapes which enhance the catalytic selectivity of the enzymes toward specific reagents.

Antibodies are another subclass of proteins. Each antibody molecule is made up of four peptide chains joined by disulfide bonds into a generally Y-shaped molecule. Antibodies, also called immunoglobulins, are produced by B cells as a primary immune defense. Each antibody has a unique binding site that can combine with a complementary site of a foreign antigen.

The carboxyl groups and the amine groups which are present in every protein may be utilized to attach the protein to a solid carrier substrate. It is preferred that the proteins be attached to the substrate by means of a covalent bond. Porous glass, ceramics, charcoal, cellulose, and synthetic polymers have successfully been used as carrier substrate materials for covalent attachment. The substrate need not be permeable to all components dissolved in a surrounding bulk liquid layer. It is preferred that the protein is immobilized throughout the substrate in a substantially uniform distribution.

The protein, such as an enzyme or antibody, is covalently bonded with a functional group which is either added to the porous carrier substrate or, if already present, activated. For instance, amino silanes can attach to ceramic substrates and then undergo reaction with glutaraldehyde, leaving an exposed carbonyl group which can then react with the amino group of an enzyme to effect immobilization. Similarly, pairs of hydroxy groups present in solid polysaccharide substrates can be treated with cyanogen bromide to produce an unsaturated carbon to nitrogen bond which can serve as a functional group for enzyme attachment. The enzyme covalent bond can also be made through diazonium salts or made directly to anhydride groups. Alternatively, the enzyme can be simply adsorbed to the carrier substrate material. Additionally, the enzyme can be bound to the carrier substrate material by electrostatic attraction, as in ionic bonding.

In a preferred embodiment, the covalent bond is prepared by hydrolyzing peptide bonds which exist in nylon polymers. Aqueous acid solutions such as aqueous hydrochloric acid can hydrolyze the bond. The result is a nylon matrix having an amine group which can be further extended by attaching a bifunctional molecule such as glutaraldehyde. Attachment of the bifunctional molecule will leave a terminal carbonyl group which can form a covalent bond with the amino group of an enzyme.

Especially preferred carrier substrate materials are commercially available polyvinylidine difluoride preactivated membranes such as an Immobilon ™ membrane available from Millipore of Waltham, Mass., and an Immunodyne ™ membrane available from Pall of Glen Cove, N.Y.

Virtually any protein can be covalently bonded to the carrier substrate. Examples of enzymes that may be covalently bonded are glucose oxidase, urease, creatinine deiminase, alcohol oxidase, glutamate oxidase, sarcosine oxidase, leucine dehydrogenase, creatinine amidohydrolase, creatine amidinohydrolase, lysine oxidase, trypsin, glutamate dehydrogenase, lactate oxidase, lactate dehydrogenase, and hexokinase. Good results have been obtained with glucose oxidase, urease, and creatinine deiminase. The nature of the reactants will dictate which enzymes should be utilized.

The concentration of enzymes is usually not expressed in molarity because the molecular formulae for many enzymes are simply unknown. Instead, enzyme concentration is commonly expressed in international units. The international unit (IU) of an enzyme is defined as the amount of enzyme that produces one micromole of a reaction product in one minute under defined reaction conditions. The mass of enzyme associated with a given number of international units will vary according to source, depending on the purity and activity of the enzyme used.

Useful protein molecules possess an active site. Each reagent molecule must first diffuse through an external layer of bulk solution to reach the substrate. Then the reagent molecule must diffuse inside the porous carrier substrate through micropores to reach the active site. At the active site, it is believed that the protein molecule and the reagent molecule align in a shape selective manner to form a transient reaction intermediary complex. After the reaction is complete, reaction product molecules diffuse inside the substrate to reach the bulk solution layer, then the molecules diffuse outside the substrate across the bulk solution.

Diffusion resistance inside the substrate pores is therefore a critical factor in the apparent activity of proteins immobilized in porous carriers. A decrease in diffusion resistance will be observed as an increase in protein catalytic activity per unit of carrier surface or carrier mass. Conversely, a decrease in the number of protein molecules available for reaction will be observed as a decrease in apparent activity.

The porous substrate of the instant invention is preferably in the form of a flat sheet. It is especially preferred that the carrier is in the form of a membrane. Membrane is defined as a thin flexible layer. Porous, semipermeable membranes made from synthetic polymer materials are especially preferred.

It is possible to manufacture membranes containing a relatively high concentration of polar functional groups by casting a polymer membrane, such as a polyamide membrane, while simultaneously casting a surface modifying polymer having functional polar groups in abundance. Useful surface modifying polymers for this purpose are polymers containing substantial proportions of ionizable, acidic functional polar groups. Illustrative examples are carboxyl, sulphonic, phenolic, amine, thio carbonyl, phosphene, and phosphoryl groups. The instant invention can be applied to such surface-modified polymer membranes, irrespective of the method of introduction of the functional groups. Alternatively, unfunctionalized membranes capable of adsorbing enzyme can also be used The porous carrier also comprises a substrate. The substrate may be any compressible solid which possesses a large number of internal micropores upon which functional groups may be attached and which can exist in a compressed state and an uncompressed state. The micropores need not be cylindrical in shape. The invention is applicable to substrates having micropores which are tortuous or sponge-like in shape. By a compressed state is meant that the substrate may be physically compressed, between inelastic surfaces for example, with the result that external dimensions of the substrate are reduced with respect to an uncompressed state. The uncompressed state is the state in which the membrane was originally manufactured. It is preferred that the membrane remain irreversibly compressed after pressure is applied and released.

An especially preferred substrate is made from polyamide resins. In particular, copolymers of hexamethylene diamine and adipic acid (Nylon 66), copolymers of hexamethylene diamine and sebacic acid (Nylon 610), and homopolymers of poly-e-caprolactum (Nylon 6) are preferred. In a typical process for manufacturing such membranes the polyamide resin is dissolved in a solvent such as formic acid and a nonsolvent such as water is added under controlled conditions of agitation to achieve nucleation of the solution. The nucleated solution is then cast onto a solid sheet or web in the form of a film. This film is contacted and diluted by a liquid non-solvent system. The polyamide resin thereupon precipitates forming a membrane sheet which can be washed to remove the solvent liquid. The membrane can then be stripped from the solid sheet. Alternatively, if the solid sheet is porous it can be incorporated in the membrane to serve as a permanent support.

The most useful membranes are those which have a pore size in the range of about 0.01 micron to about 10 microns, where a micron is defined as $1 \times 10^{-6}$ meter. The range of about 0.1 to about 2 microns is especially preferred. The ratio of the total volume of internal micropores expressed as a percentage of the total volume of the substrate is defined as the percent porosity of the substrate. It is preferred that the substrate be in the range of about 30% porous to about 80% porous in its uncompressed state. Useful substrates in the compressed state are typically in the range of about 10% porous to about 50% porous. In practice, the membrane containing immobilized protein may be utilized in tandem with one or more other membranes which may possess different physical and diffusional characteristics.

The density of the substrate in its compressed state is in the range of about 1.25 to about 5.0 times the density of the substrate in an uncompressed state. The uncompressed state is defined as the state in which the porous carrier is originally manufactured. For a polymer membrane this would usually be the state existing after the membrane had been washed and dried. The compressed state is achieved by physically pressing upon the membrane in its uncompressed state. Preferably, two inelastic flat surfaces are used to compress the carrier and the resulting form of the compressed carrier is a flat sheet with a thickness less than that of the uncompressed carrier.

During compression, the percent porosity of the carrier substrate decreases, typically, to a value which is about one-half that of the percent porosity in the uncompressed state. It is believed that some internal micropores are crushed or constricted by the compression. However, it appears that the length of other diffusion paths from bulk solution layer to enzyme-active sites are effectively decreased. A net decrease in overall diffusional resistance through the substrate is observed.

In a preferred embodiment, the substrate is only compressed in one dimension, that is, its least dimension in the sheet form. In that case, the thickness of the substrate in the compressed state should be in the range of about 0.2 to about 0 8 times the thickness of the substrate in the uncompressed state. As an illustrative example, for a membrane in sheet form that had a thickness of 145 microns to be compressed into a final state of 46 microns, the thickness of the compressed state would be 0.32 times that of the original uncompressed state.

The shape of the polypeptide chain which forms the enzyme or antibody is critical to its function as an organic catalyst. Many proteins are shape-selective. That is, they recognize specific reagents which have shapes that complement the shape of the enzyme peptide chain. If the peptide chain changes its shape so as to lose its specificity toward certain reagents, the protein is said to be denatured. To avoid denaturing the protein, it is necessary to avoid subjecting the protein to extreme heat or cold, to gross changes in pH, to harsh chemicals, and to dehydration. In many cases, it is desirable to keep biologically active proteins in contact with an aqueous liquid phase at all times. Accordingly, it is within the scope of the present invention to form the compressed carrier substrate by compressing the uncompressed state after the protein has been absorbed or covalently attached and while the protein is in contact with a stabilizing liquid phase. Additionally, when choosing the method of adsorption or covalent attachment for the protein, harsh chemicals and chemicals which fail to wash freely from the substrate should be avoided in order to minimize the possibility of such chemicals later denaturing the protein.

The following examples are intended to illustrate particular embodiments of the invention and are not intended to limit the scope of the claims in any way.

EXAMPLE I

In this example, biologically active enzymes were immobilized on the internal surface of an uncompressed, commercially available membrane. The membrane employed was a preactivated polyvinylidine difluoride membrane obtained from Millipore of Waltham, Mass., under the trade name Immobilon AV Affinity Membrane. The membrane contained polar functional groups capable of covalently binding enzymes. As delivered from the manufacturer, the functional groups were in a suitably activated carbonyl state to bind enzymes without further chemical preparation. The membrane in its uncompressed state was about 80% porous and had an average pore size of 0.65 microns.

Glucose oxidase enzyme was immobilized upon the uncompressed membrane. An amount of glucose oxidase sufficient to place about 100 micrograms of enzyme within each square centimeter of membrane was dissolved in an aqueous solution containing a buffer which held the solution at approximately pH 7. The aqueous enzyme solution was applied to both sides of the membrane and allowed to dry completely. Finally, the membrane was rinsed several times with buffer solution. The immobilized enzyme membrane produced by this procedure was designated "membrane A".

EXAMPLE II

Samples of the membrane produced in EXAMPLE I, designated membrane A, were compressed between flat, inelastic surfaces for time periods of 3 minutes at constant applied pressures ranging from 0 to 1.2 metric tons/cm². The thickness of each compressed membrane sample was measured and recorded 1 minute after release of pressure. The thicknesses of the compressed membrane samples were substantially the same at 1 minute after pressure release as they were at 14 hours after pressure release. The measurements recorded 1 minute after release are presented in TABLE 2.

TABLE 2

Thickness of Membrane A Samples After 3 Minutes of Applied Pressure and Release

| Applied Pressure (Metric Tons/cm$^2$) | Membrane Thickness ($1 \times 10^{-6}$ m.) |
| --- | --- |
| 0 | 136 |
| 0.21 | 108 |
| 0.31 | 100 |
| 0.43 | 95 |
| 0.79 | 85 |
| 0.80 | 88 |
| 0.87 | 85 |
| 1.06 | 77 |
| 1.07 | 83 |
| 1.23 | 80 |

Inspection of TABLE 2 reveals that membrane A can be compressed to about 0.66 times its original thickness by applying 0.8 metric tons/cm$^2$ of pressure to the membrane for a period of about 3 minutes. Applied pressures of greater than 0.8 metric tons/cm$^2$ produced very little additional decrease in the thickness of membrane A.

EXAMPLE III

Samples of membrane A were compressed with an applied pressure of approximately 1 metric ton/cm$^2$ for varying lengths of time. The thicknesses of the compressed membrane samples were measured and recorded 14 hours after release of pressure. The data which was collected demonstrates the eff~~ ~t of varying the length of time during which pressure was applied. It is summarized in TABLE 3.

TABLE 3

Thickness of Membrane A Samples After Compression at 0.8 to 1.4 Metric Tons/cm$^2$ for Varying Lengths of Time and Release

| Time of Applied Pressure (Minutes) | Thickness ($1 \times 10^{-6}$ m.) |
| --- | --- |
| 0 | 136 |
| 3 | 91* |
| 10 | 84 |
| 30 | 84+ |

*average of 6 trials
+performed with 1.4 metric ton/cm$^{-2}$

The data shown in TABLE 3 indicates that a substantial amount of compression may be accomplished within 3 minutes at an applied pressure of approximately 1 metric ton/cm. Little further decrease in the thickness of membrane A occurred after 10 minutes of applied pressure.

EXAMPLE IV

Samples of membrane B, a synthetic membrane which is commercially available under the trade name Ultrabind from Gelman of Ann Arbor, Mich., were compressed for a period of 3 minutes with various levels of constant applied pressure. The samples of membrane B contained no immobilized enzyme. Compressed membrane sample thicknesses were measured and recorded 1 minute after release. The thicknesses were substantially the same at 1 minute, at 1 hour, and at 14 hours after release. The results recorded at 1 minute after release are shown in TABLE 4.

TABLE 4

Thickness of Membrane B Samples After 3 Minutes of Applied Pressure and Release

| Applied Pressure (metric tons/cm$^2$) | Membrane Thickness After Release ($1 \times 10^{-6}$ m.) |
| --- | --- |
| 0 | 144 |
| 0.25 | 54 |
| 0.50 | 49 |
| 0.75 | 44 |
| 1.00 | 42 |
| 1.25 | 43 |
| 1.50 | 40 |
| 1.75 | 42 |
| 2.00 | 41 |

The data in TABLE 4 demonstrates that membrane B can be compressed to about 0.30 times its original thickness by applying a pressure of 0.8 metric tons for a period of 3 minutes. Little further increase in compression was achieved by increasing the applied pressure over 0.8 metric tons/cm$^2$.

EXAMPLE V

This Example tests membrane samples containing an immobilized glucose oxidase enzyme, prepared by the method described in EXAMPLE I, to determine diffusion resistance in various states of compression. Each membrane sample was installed in an amperometric sensor. The membrane was in contact with a glucose solution containing dissolved oxygen. Another surface of the enzyme membrane was in contact with an electrically conductive electrode connected to the amperometric sensor.

In operation, glucose and oxygen in a buffered solution diffused into the enzyme membrane to contact the glucose oxidase. Under the influence of the enzyme catalyst, the glucose and oxygen reacted to produce gluconolactone and hydrogen peroxide. The resulting hydrogen peroxide diffused to the electrode where it dissociated to produce diatomic oxygen, hydrogen ion, and an electric current. The quantity of electric current detected at the electrode quantitatively indicated the amount and the speed of the glucose oxidation reaction in the enzyme membrane.

The diffusion resistance testing was conducted in flow-injection mode. That is, flow of a buffer solution was maintained continuously through the liquid side of the amperometric sensor. At intervals, glucose-rich buffer solution was also injected into the flow cell. Throughout the experiment, a steady flow of 485 microliters per minute was maintained through the flow cell. Injections of glucose solution were made in volumes of 100 microliters each. After each injection, the amperometric detector was allowed to return to equilibrium before another injection of glucose-rich buffer solution was made.

The strip chart recorder connected to the amperometric detector produced a reproducible peak having a maximum height which corresponded to a maximum current through the detector. Response time was calculated as the time from the glucose-rich solution injection to the time at which the maximum peak height was recorded. The width of the observed peak measured at one-half the maximum height was also observed and recorded. Finally, recovery time was defined to be the period of time necessary for the peak to return to 5% or less of maximum peak height as measured from the time of glucose-rich solution injection.

Two immobilized enzyme carriers of the type designated membrane A were pressed into varying states of compression using the method described in EXAMPLE II above. One was not compressed at all, maintaining a compression factor of 1.0 throughout the test. The other was compressed to 0.66 times its original thickness. Each was exposed to 100 microliters of glucose solution as described above in this EXAMPLE. The response time and the recovery times of the two membranes are summarized in TABLE 5 below.

TABLE 5

| Compression Factor | Compressed Immobilized Membrane Thickness ($1 \times 10^{-6}$ m.) | Response Time (seconds) | Recovery Time (seconds) |
|---|---|---|---|
| 1.0 | 136 | 37 | 103 |
| 0.68 | 91 | 30* | 70* |

*average of three trials

Inspection of TABLE 5 reveals that a superior glucose sensing electrode can be constructed which uses an immobilized enzyme carrier membrane sample that has been compressed to 0.68 times its original thickness. The 0.68 compression factor membrane sample exhibited a relatively quicker response time and a shorter recovery time.

Response time and recovery time are indicators of the diffusion resistance of the membrane toward the reagent glucose. It is believed that the compression of the membrane restricted access to some enzyme molecules by crushing micropores in the 0.66 compression factor test, but that the compression also reduced the effective diffusion path lengths to and from the enzyme molecules which were still accessible. A combination of the two effects seems to be responsible for the net overall decrease in diffusion resistance observed in the 0.66 compression factor test. The compressed enzyme membrane sample, with a compression factor of 0.66, demonstrated a relatively lower response time and a lower recovery time of the two membrane samples tested.

EXAMPLE VI

This example tests samples containing immobilized urease for diffusion resistance. Urease enzyme was immobilized upon several samples of compressed Immobilon ™ by adding 136 micrograms of urease per square centimeter in an aqueous buffer of pH 7.4. The membranes were allowed to dry completely and rinsed with buffer. The membranes were in the shape of squares measuring approximately 4 square centimeters on one face. Selected samples were compressed at 8 metric tons for five minutes.

Each membrane was installed in an ion-selective electrode. One side of the membrane was in contact with a urea-containing solution. The other side of the enzyme membrane was in contact with an ionophore gel, selective for ammonium ion.

In operation, urea in a buffered solution diffused into the enzyme membrane to contact the enzyme catalyst. At the enzyme catalyst, the urea hydrolyzed to produce ammonium ions and carbon dioxide. The resulting ammonium ions further diffused to the ionophore gel where the ammonium ions complexed the ionophore, producing a change in a potential gradient across the ionophore gel. The change quantitatively indicated the amount and speed of a urea hydrolysis reaction in the enzyme membrane.

This diffusion resistance test was conducted in a flow-injection mode. That is, flow of a buffer solution was maintained continuously though the liquid side of the ion-selective electrode cell. At intervals, urea-rich buffer solution as also injected into the flow cell. Throughout the experiment, a steady flow of 485 microliters per minute was maintained through the flow cell. Injections of urea solution were made in volumes of 100 microliters each. After each injection, the ion-selective electrode was allowed to return to equilibrium before another injection of urea-rich buffer solution was made.

A strip chart recorder connected to a pH meter produced a peak having a maximum height which corresponds to a maximum electrical potential change across the ionophore gel. Response time is calculated as the time from the urea-rich solution injection to the time at which the maximum height was observed and recorded. Recovery time was defined to be the period of time necessary for the peak to return to 5% or less of the maximum peak height as measured from the time of urea-rich solution injection.

The response times and recovery times of four uncompressed test membranes and two compressed membranes are summarized in Table 6.

TABLE 6

| | Response Time (seconds) | Recovery Time (seconds) | Compressed Membrane |
|---|---|---|---|
| 1 | 45 | 220 | No |
| 2 | 56 | 756 | No |
| 3 | 65 | 295 | No |
| 4 | 48 | 180,192 | No,No (two trials) |
| 5 | 46,54,72 | 126,180,324 | Yes,Yes,Yes (three trials) |
| 6 | 50,38 | 150,102 | Yes,Yes (two trials) |

Inspection of Table 6 reveals that the recovery time was generally faster with the compressed membranes, indicating that the ammonium ion more quickly diffused out of the membrane. Therefore, a superior urea sensing electrode can be constructed which uses a compressed enzyme carrier membrane.

EXAMPLE VII

This hypothetical example will serve to illustrate how a biologically active antibody can be immobilized on internal surfaces of a compressed porous membrane and an uncompressed porous membrane. The compressed membrane is prepared by application of sufficient force to irreversibly decrease the thickness of the membrane from about 136 micrometers to 90 micrometers. One surface of the membrane is exposed to a solution of an antigen and an antigen-enzyme conjugate for a predetermined amount of time. The surface of the membrane is subsequently exposed to a rinse solution which does not contain the antigen or the antigen-enzyme conjugate. The surface is then exposed to a solution of an enzyme substrate for a fixed amount of time. The amount of reaction product from the enzyme reaction is measured with an appropriate electrode, or by use of another type of sensing element, to determine the amount of antigen.

The surface of the membrane may, optionally, be exposed to a solution of chaotropic reagent in order to disassociate the antibody-antigen and the antibody-antigen-enzyme complexes, thereby enabling the membrane to be reused.

The amount of time required for complete removal of unbound antigen-enzyme conjugate during the rinse step is chiefly determined by the time required for unbound antigen-enzyme conjugate to diffuse out of the membrane. Likewise, the amount of time required for complete removal of unbound antigen and antigen-enzyme conjugate during the chaotropic reagent regeneration step is chiefly determined by diffusion of unbound antigen-enzyme conjugate of the membrane. Time required for diffusion is believed to be proportional to the diffusion distance squared. Compressing the membrane from 136 micrometers to 90 micrometers decreases the diffusion distance by 34% and decreases the time required for diffusionally related processes by 56%.

What is claimed is:

1. A process for making a porous carrier containing an immobilized protein, which comprises:
    attaching a plurality of polar functional groups to an internal surface which defines a plurality of micropores distributed throughout a porous membrane substrate so that the substrate is about 30 to about 80 volume percent porous;
    covalently bonding a plurality of selective proteins to at least a portion of the functional groups; and
    physically compressing the membrane substrate to produce an irreversibly compressed membrane substrate having a pore size of at least about 0.01 micron, a porosity of about 10 to about 50 volume percent, a density of about 1.25 to about 5.0 times the density of the membrane substrate before compressing and a thickness of about 0.2 to about 0.8 times the thickness of the membrane substrate before the compressing.

2. The process of claim 1 wherein the membrane substrate comprises polyvinylidine difluoride.

3. The process of claim 1 wherein the protein is immobilized throughout the membrane substrate in a substantially uniform distribution.

4. The process of claim 1 wherein the protein is glucose oxidase.

5. The process of claim 1 wherein the protein is urease.

6. The process of claim 1 wherein the protein is creatinine deiminase.

7. The process of claim 1 wherein the protein is an antibody.

8. A porous carrier containing an immobilized protein prepared by the process of claim 1.

9. The process of claim 8 wherein the membrane substrate comprises polyvinylidine difluoride.

10. The process of claim 1 wherein the protein is immobilized throughout the membrane substrate in a substantially uniform distribution.

11. The process of claim 8 wherein the protein is an antibody.

12. The process of claim 8 wherein the protein is glucose oxidase.

13. The process of claim 8 wherein the protein is urease.

14. The process of claim 8 wherein the protein is creatinine deiminase.

* * * * *